United States Patent [19]

Martel et al.

[11] 4,350,637
[45] Sep. 21, 1982

[54] SUBSTITUTED LACTONES OF AMINO ACIDS

[75] Inventors: Jacques Martel, Bondy; Jean Tessier, Vincennes; André Teche, Paris, all of France

[73] Assignee: Roussel Uclaf, Paris, France

[21] Appl. No.: 212,569

[22] Filed: Dec. 3, 1980

[30] Foreign Application Priority Data

Dec. 10, 1979 [FR] France .............................. 79 30201

[51] Int. Cl.³ .................. C07D 307/77; C07D 307/32; C07D 309/30
[52] U.S. Cl. .................................. 549/304; 548/525; 549/293; 549/321
[58] Field of Search ...................... 260/343.3 R, 343.5, 260/343.6

[56] References Cited

U.S. PATENT DOCUMENTS 3,992,416 11/1976 Bolz et al. .................... 260/343.3 R

FOREIGN PATENT DOCUMENTS 589759 12/1959 Canada ........................ 260/343.3 R
1081471 5/1960 Fed. Rep. of Germany .
2510714 9/1976 Fed. Rep. of Germany ... 260/343.3 R
2910417 3/1978 Fed. Rep. of Germany ... 260/343.3 R

*Primary Examiner*—Jane T. Fan
*Attorney, Agent, or Firm*—Hammond & Littell, Weissenberger and Muserlian

[57] ABSTRACT

Novel substituted lactones of amino acids in all their possible stereoisomeric forms or mixtures thereof of the formula

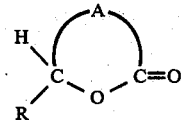

wherein A is a hydrocarbon chain of 1 to 10 chain members containing one or more heteroatoms and one or more unsaturations and the chain members being a mono- or polycyclic system or comprises a system of spiro or endo type and may contain one or more chiral atoms or the lactone copula can present a supplementary chirality due to the asymmetric spatial configuration of the molecule make up and R is selected from the group consisting of:

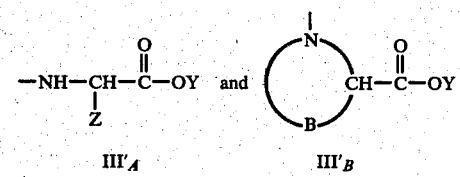

wherein Z is the organic remainder of an amino acid of the formula:

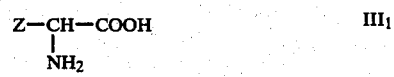

Y is derived from a primary, secondary or tertiary alcohol of the formula Y-OH and B is the remainder of a heterocycle amino acid of 3 to 6 carbon atoms of the formula:

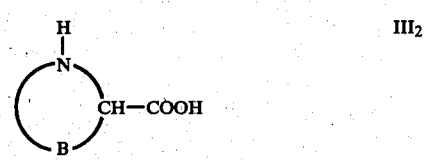

and their preparation and their use for the resolution of amino acids.

8 Claims, No Drawings

SUBSTITUTED LACTONES OF AMINO ACIDS

STATE OF THE ART

Related compounds are described in German Pat. Nos. 2,510,714 and 1,081,471 and copending, commonly assigned U.S. patent application Ser. No. 021,833 filed Mar. 19, 1979.

OBJECTS OF THE INVENTION

It is an object of the invention to provide the novel lactones of formula I and a novel process for their preparation.

It is another object of the invention to provide a novel process for the resolution of amino acids.

These and other objects and advantages of the invention will become obvious from the following detailed description.

THE INVENTION

The novel lactones of the invention are substituted lactones of amino acids in all their possible stereoisomeric forms or mixtures thereof of the formula:

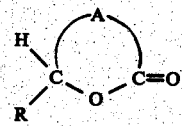
I wherein A is a hydrocarbon chain of 1 to 10 chain members containing one or more heteroatoms and one or more unsaturations and the chain members being a mono- or polycyclic sytem or comprises a system of spiro or endo type and may contain one or more chiral atoms or the lactone copula can present a supplementary chirality due to the asymetric spatial configuration of the molecule make up and R is selected from the group consisting of:

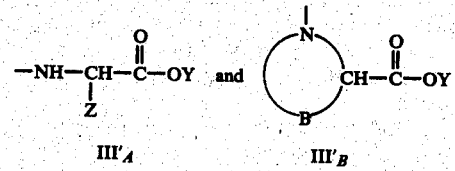

III'$_A$        III'$_B$ wherein Z is the organic remainder of an amino acid of the formula:

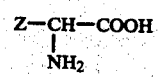
III$_1$

Y is derived from a primary, secondary or tertiary alcohol of the formula Y-OH and B is the remainder of a heterocycle amino acid of 3 to 6 carbon atoms of the formula:

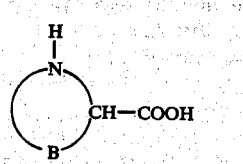
III$_2$

The esters of amino acids of the formula

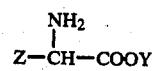

are denominated herein as formula III$_A$ and esters of cyclic amino acids of the formula:

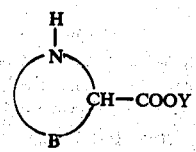

are denominated as formula III$_B$. The amino acids of formula:

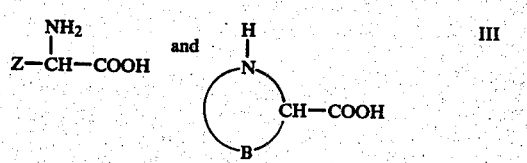
III include the naturally occuring amino acids, notably those listed in Chem. Abs., Vol. 76, p. 901 and also include synthetic amino acids, especially those listed in "Amino acids, peptides and proteins," Vol. 2, page 10, Specialist Periodic Reports and The Chemical Society, Burlington House, London W1 VOBN 1970 Edition or Vol. 1, p. 13, 1969 edition.

Among the preferred compounds of formula I are those wherein the A chain contains at least one asymetric carbon atom and in which the 2 atoms or different radicals which substitute the atom of asymmetric carbon are independently selected from one or other of the following groups: (a) groups are hydrogen, halogens, nitro, alkyl of 1 to 10 carbon atoms, cycloalkyl of 3 to 6 carbon atoms, phenyl, phenyl substituted with at least one member of the group consisting of halogen, alkyl of 1 to 6 carbon atoms, carboxyl, —CN, —CHO, acyl of an organic carboxylic acid of 1 to 6 carbon atoms,

and alkylthio and alkoxy of 1 to 6 carbon atoms; (b) a group selected from the group consisting of

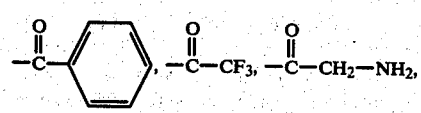

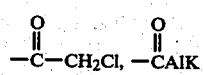

where ALK is alkyl of 1 to 6 carbon atoms and —NH—X$_1$ where X$_1$ is hydrogen alkyl of 1 to 6 carbon atoms, (c) the group of the formula

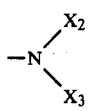

where $X_2$ and $X_3$ are individually alkyl of 1 to 6 carbon atoms or taken together with the nitrogen atom form a heterocycle of 6 atoms or $X_3$ is benzyl and $X_2$ is carboxyl.

Other preferred compounds of formula I are those wherein A is an aliphatic hydrocarbon of 2 to 3 carbon atoms, those wherein A is an aliphatic hydrocarbon interrupted by one or more heteroatoms, those wherein A is an aliphatic hydrocarbon containing a double bond, those wherein A is a monocyclic hydrocarbon of 3 to 6 carbon atoms optionally containing one unsaturation, those wherein A is a bicyclic hydrocarbon containing 5 to 10 carbon atoms optionally containing one unsaturation, those wherein A is

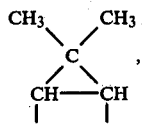

those wherein A is

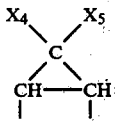

and $X_4$ and $X_5$ are individually selected from the group consisting of hydrogen, fluorine, chlorine, bromine and alkyl of 2 to 6 carbon atoms or taken together with the carbon atoms to which they are attached from a carbon homocycle of 3 to 7 carbon atoms and those wherein A is

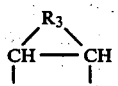

wherein $R_3$ is selected from group consisting of —O—, —S—, —NH— and —NR$_4$— and $R_4$ is alkyl of 1 to 6 carbon atoms.

Among the particularly preferred compounds of the invention of formula I are those wherein Y is derived from a primary aliphatic alcohol of 1 to 12 carbon atoms, those wherein Y is derived from a primary cycloaliphatic alcohol of 4 to 8 carbon atoms, those wherein Y is derived from benzyl alcohol, those wherein R is derived from an ester of a natural amino acid, those wherein R is derived from an ester of a natural amino acid of the group consisting of leucine, proline, phenylalanine and methionine and those wherein R is derived from an ester of a synthetic amino acid.

Among the specific compounds of formula I are the various possible stereoisomeric forms and mixtures thereof of benzyl (αR,3R,3aR,4S,7R,7aS)α-[(1-oxo-3a,4,7,7a-tetrahydro-1H, 3H-4,7-methanoisobenzofuran-3-yl)-amino]-isohexanoate, benzyl (αS,3S,-3aS,4R,7S,7aR) α-[(1-oxo-3a,4,7,7a-tetrahydro-1H, 3H-4,7-methanoisobenzofuran-3-yl)-amino]-isohexanoate, benzyl (αR,3S,3aS,4R,7S,7aR)α-(1-oxo-3a,4,7,7a-tetrahydro-1H, 3H-4,7-methanoisobenzofuran-3-yl)-D prolinate, benzyl (αR,3R,3aR,4S,7R,7aS) α-(1-oxo-3a,4,7,7a-tetrahydro-1H, 3H-4,7-methanoisobenzofuran-3-yl)-L-prolinate, methyl (αR,3R,3aR,4S,7R,7aS)α-[(1-oxo-3a,4,7,7a-tetrahydro-1H,3H-4,7-methanoisobenzofuran-3-yl)-amino]-phenylpropanoate, methyl (αS,3S,3aS,4R,7S,7aR)α-[(1-oxo 3a,4,7,7a-tetrahydro-1H, 3H-4,7-methanoisobenzofuran-3-yl)-amino]-phenylpropanoate, methyl (3S,3aS,4R,7S,7aR)α-(1-oxo-3a,4,7,7a-tetrahydro-1H, 3H-4,7-methanoisobenzofuran-3-yl)-L-methioninate and methyl (3R,3aR,4S,7R,7aS)α-(1-oxo-3a,4,7,7a-tetrahydro-1H, 3H,4,7-methanoisobenzofuran-3yl)-L-methioninate.

The novel process of the invention for the preparation of compounds of formula I comprises reacting a compound of the formula:

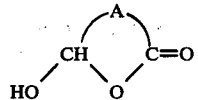

wherein A has the above definition with an ester of an amino acid of formula III$_A$ or III$_B$ to obtain the corresponding compound of formula I or otherwise denominated as formula I$_A$ where the chiral atoms possess a well defined configuration when the lactonic copula and the ester of the amino acid possess one or more chiral atom of well defined configuration or otherwise denominated as formula I$_B$ where it acts as a mixture of diastereoisomers, the lactone being a well defined optical isomer and the chiral center or centers of the ester of the amino acid not having an univocal configuration or otherwise denominated as formula I$_C$ when it acts as a mixture of diastereoisomers, the ester of the amino acid being a well defined optical isomer and the chiral atoms of the lactonic copula not having all of an univocal configuration, then, if necessary separating by a physical method the diastereoisomeric compounds contained either in the mixtures of type I$_B$ or in the mixtures of type I$_C$ wherein the chiral centers are all of an univocal configuration.

A preferred form of the process of the invention for the preparation of the compounds of formula I comprises reacting the ester of an amino acid of formula III$_A$ and the lactone of formula II while removing the water of reaction by physical means, especially by azeotropic distillation with a solvent selected from the group consisting of chlorinated solvents, aromatic hydrocarbons, aliphatic hydrocarbons and ethers, more especially by distillation under reduced pressure. The separation of the diastereoisomeric compounds is preferably effected by crystallization or chromatography.

The lactonic compounds of formula II are preferably selected from the group consisting of (1R,5S) 6,6-dimethyl-4(R)-hydroxy-3-oxabicyclo (3,1,0) hexan-2-one, (1S,5R) 6,6-dimethyl-4(S)-hydroxy-3-oxabicyclo (3,1,0) hexan-2-one, (3R,3aR,4S,7R,7aS) 3-hydroxy-tetrahydro-4,7-methanoisobenzofuran-1-one and (3S,3aS,4R,7S,7aR) 3-hydroxy-tetrahydro-4,7-methanoisobenzofuran-1-one.

If the chiral atom or atoms of the lactonic copula of formula II are each of (R) or (S) determined steric configuration when the asymmetric carbon atom or atoms of the ester of the amino acid of formula III$_A$ or III$_B$ are individually of (R) or (S) determined steric configuration, the compounds of formula I$_A$ are directly obtained with retention of the configurations. When the esters of the amino acids of formula III$_A$ or III$_B$ possessing one or more unresolved asymmetric carbon atom are used in the process of the invention, a mixture of diastereoisomeric compounds of formula I denominated as formula I$_B$ are obtained which can be separated by a physical treatment, especially by chromatography or by crystallization from a solvent, with the latter being especially interesting.

After separation of diastereoisomers of formula I$_B$, for example, after separation of formula I$_A$, a simple hydrolysis permits the obtaining of esters of amino acids of formula III$_A$ or III$_B$ resolved about the racemic asymetric carbon atoms which are initially present. When the ester of amino acids of formula III$_A$ or III$_B$ possess m nonresolved chiral centers, it forms 2 m analogous diastereoisomers of formula I$_A$ which can eventually separated into the individual ones.

Otherwise, one recovers the lactonic compounds of formula II used of which the chiral atoms have the (R) or (S) determined steric configuration which exists in the starting compound. It is understood that the preceding considerations apply in the same manner to the esters of the amino acids of formula III$_A$ and III$_B$.

When the lactonic copula has the (RS) racemic configuration due to one or more unresolved chiral centers, one obtains a mixture of diastereoisomeric compounds of formula I denominated as formula I$_C$ which can be separated by a physical treatment, especially by chromatography or crystallization from a solvent, preferably the latter.

After separation of diastereoisomers of formula I into formula I$_C$, for example after separation of formula I$_A$, a simple hydrolysis permits the obtaining of resolved lactonic compounds due to (RS) racemic configuration of chiral atoms which are initially present. When the lactonic copula possesses n non-resolved chiral centers, it forms 2 n diastereoisomers of formula I$_A$ which eventually can be separated into the individual ones.

Otherwise, one recovers the ester of amino acids of formula III$_A$ or III$_B$ due to the asymmetric carbon atoms of (R) or (S) determined configuration which exists in the starting amino acids of formulae III$_1$ or III$_2$. It is understood that the preceding considerations concerning the esters of amino acids of formula I$_A$ are equally applicable to the esters of formula III$_B$.

In all of the preceding discussion, the presence of at least one resolved or unresolved chiral center in the compounds of formulae II, III$_1$ or III$_2$ implies the following different possibilities: either the chiral centers do not possess an univocal configuration of (R) or (S) and the compound of formula I is a mixture of racemates of enantiomers or one part of the chiral centers possesses an univocal (R) or (S) configuration and the compound of formula I is a mixture of diastereoisomers or all the chiral centers have an univocal (R) or (S) configuration and the compound of formula I are of well defined optical isomers.

It is to be emphasized that a single chiral atom of the indispensable lactonic compound to resolve amino acids (in the ester form) or to resolve the lactone itself is the one that is situated in the α-position to the endocyclic oxygen, the other supplementary chiral carbon atoms can exist in the lateral chain A and aren't indispensable for effecting the resolutions.

In a particularly preferred embodiment of the process of the invention, the lactonic compound is (3R,3aR,4S,7R,7aS) 3-hydroxy-tetrahydro-4,7-methanoisobenzofuran-1-one or (3S,3aS,4R,7S,7aR) 3-hydroxy-tetrahydro-4,7-methano-isobenzofuran-1-one and the compounds of formula I are esters of amino acids selected from the group consisting of benzyl leucinate, benzyl prolinate, methyl phenylalaninate and methyl methioninate.

The novel process for the invention for the resolution of compounds of formula II or compounds of formula III comprises subjecting the diastereoisomeric compounds isolated from mixtures of formula I$_C$ or I$_B$ to acid hydrolysis in an aqueous medium to either recover compounds of formula II with asymmetric carbon atoms of an univocal configuration or subjecting the resulting ester of an amino acid of formula III to the action of a hydrolysis agent to hydrolyze the ester group and recovering the desired amino acid with asymmetric carbon atoms of an univocal configuration.

In this process, the ester of the amino acid possesses an unresolved asymmetric center and the lactone of formula II possesses at least one chiral center of the (R) or (S) defined configuration. The two said compounds are reacted to form a mixture of the two diastereoisomers of formula I$_A$ (I$_D$ and I$_E$) which is then separated by physical means such as chromatography or crystallization. The individual isomers of formula I$_D$ and I$_E$ are then subjected to hydrolysis to obtain the corresponding isomer of the ester of the amino acid of formula III$_A$ or III$_B$ which is then subjected to hydrolysis to remove the ester group resulting in obtaining the individual isomer of the amino acid in the (R) or (S) antipodes.

If the hydrolysis of the esters of formula III$_A$ or III$_B$ is effected with an alkaline agent in an aqueous medium, the amino acid of formula III$_1$ or III$_2$ is recovered in the form of its salt. The removal of the ester group may also be effected by hydrogenolysis with hydrogen in the presence of a catalyst. Other classical methods may also be used.

In a similar manner, the starting lactone of formula II has chiral centers presenting the configuration corresponding to a racemate and is reacted with a prefectly defined optical isomer of an ester of an amino acid of formula III$_A$ or III$_B$ to obtain 2 compounds of formula I$_A$ (I$_F$ and I$_G$) which are separated by physical methods such as chromatography or crystallization. The individual isomers of formula I$_F$ or I$_G$ have an antipodal configuration and are then subjected to acid hydrolysis to obtain the resolved lactone of formula II in its antipodal form.

In the process of the preparation of the compounds of formula I of the invention and in the use of the compounds, the esters of the amino acids of formula III$_A$ or III$_B$ and the amino acids of formula III$_1$ or III$_2$ are conveniently obtained in the form of their acid addition salts, especially the hydrochloride.

In summary, the aggregate of the reactions permit either the resolution of amino acids after transformation into their esters with the lactones of formula II of a well defined configuration or the resolution of the lactones of formula II with the ester of amino acids of a well defined configuration.

The biologically used amino acids are generally used in the form of their optical isomers and the method of the invention permits the resolution of the corresponding racemic amino acids produced by synthesis. As the resolution of lactones of formula II is difficult to effect, it is welcome to find an elegant solution to the problem.

In the following examples there are described several preferred embodiments to illustrate the invention. However, it should be understood that the invention is not intended to be limited to the specific embodiments.

EXAMPLE 1

Benzyl (αR,3R,3aR,4S,7R,7aS)α-[(1-oxo-3a,4,7,7a-tetrahydro-1H, 3H-4,7-methano-isobenzofuran-3-yl)-amino]-isohexanoate STEP A: Benzyl DL leucinate A mixture of 3.93 g of the tosylate of benzyl DL leucinate, 25 ml of demineralized water, 150 ml of ether and 1.01 g of triethylamine was stirred at 20° C. for 10 minutes and the mixture was then extracted with ether. The decanted organic phase was dried and evaporated to dryness under reduced pressure to obtain 2.2 g of benzyl DL leucinate.

STEP B: Benzyl (αR,3R,3aR,4S,7R,7aS)α-[(1-oxo-3a,4,7,7a-tetrahydro-1H,3H-4,7-methano-isobenzofuran-3-yl)-amino]-isohexanoate A mixture of 2.2 g of the product of Step A and 1.66 g of (3R,3aR,4S,7R,7aS) 3-hydroxy-tetrahydro-4,7-methano-isobenzofuran-1-one with a specific rotation $[\alpha]_D^{20} = +47°$ (c=1% in chloroform) and 30 ml of benzene was refluxed with stirring for one hour while azeotropically distilling the water of reaction from the mixture and the mixture was then evaporated to dryness under reduced pressure. The residue was crystallized from about 15 ml of isopropyl ether and the mixture was iced and vacuum filtered at 10° C. to obtain 1.4 g of benzyl (αR,3R,3aR,4S,7R,7aS)α-[(1-oxo-3a,4,7,7a-tetrahydro-1H,3H-4,7-methano-isobenzofuran-3-yl)-amino]-isohexanoate melting at 88° C.

IR Spectrum (chloroform): Absorption at 3340 cm$^{-1}$ (NH); at 1760 to 1745 cm$^{-1}$ (carbonyl, γ-lactone, ester); at 1390 to 1370 cm$^{-1}$ (geminal methyls); at 698 cm$^{-1}$ (phenyl).

NMR Spectrum (CDCl$_3$): Peaks at 6.32 ppm (5- and 6-ethylenic hydrogens of lactone); at 1.32-1.45 ppm and 1.58-1.72 ppm (hydrogens of 8—CH$_2$ of lactone); at 4.68 ppm (3-hydrogen of lactone); at 2.52 ppm (hydrogen of amine); at 0.85-0.93 ppm (hydrogens of geminal methyls); at 5.2 ppm (α-hydrogens to phenyl); at 7.42 ppm (aromatic hydrogens).

Circular dichroism (dioxane):

| max. at 225 nm | Δε = +1.9 |
| max. at 260 nm | Δε = −0.03 |

EXAMPLE 2

Benzyl (αS,3S,3aS,4R,7S,7aR)α-[(1-oxo-3a,4,7,7a-tetrahydro-1H,3H-4,7-methano-isobenzofuran-3-yl)-amino]-isohexanoate Using the procedure of Step B of Example 1, a mixture of 2.2 g of benzyl DL leucinate, 1.66 g of (3S,3aS,4R,7S,7aR)-3-hydroxy-tetrahydro-4,7-methano-isobenzofuran-1-one with a specific rotation of $[\alpha]_D^{20} = -47°$ (c=1% in chloroform) and 30 ml of benzene was refluxed for 2 hours to obtain 1.4 g of benzyl (αS,3S,3aS,4R,7S,7aR(α[(1-oxo-3a,4,7,7a-tetrahydro-1H,3H-4,7-methano-isobenzofuran-3-yl)-amino]-isohexanoate melting at 88° C.

IR Spectrum (chloroform): Absorption at 3340 cm$^{-1}$ (NH); at 1760 to 1745 cm$^{-1}$ (carbonyl, γlactone, ester); at 1390-1370 cm$^{-1}$ (geminal —CH$_3$s); at 698 cm$^{-1}$ (phenyl).

NMR Spectrum (CDCl$_3$): Peaks at 6.18 ppm (5- and 6-ethylenic hydrogens of lactone); at 1.32-1.45 ppm and 1.57-1.7 ppm (hydrogens of 8—CH$_2$ of lactone); at 4.6 ppm (3-hydrogen of lactone); at 2.25 ppm (hydrogen of amine); at 0.83-0.95 ppm (hydrogens of geminal methyls); at 5.1 ppm (hydrogens α to phenyl); at 7.35 ppm (aromatic hydrogens).

Circular dichroism (dioxane):

| max. at 226 nm | Δε = −1.86 |
| max. towards 260 nm | Δε ≃ +0.01 |

EXAMPLE 3

Benzyl (αS,3S,3aS,4R,7S,7aR)α-(1-oxo-3a,4,7,7a-tetrahydro-1H,3H-4,7-methano-isobenzofuran-3-yl)-D-prolinate A mixture of 3.18 g of benzyl DL-prolinate hydrochloride, 3 ml of demineralized water, 25 ml of benzene and 1.34 g of triethylamine was stirred at 20° C. for one hour and the decanted organic phase was washed with water, dried and evaporated to dryness to obtain 2.6 g of benzyl DL-prolinate in the form of a colorless oil.

A mixture of 2.6 g of the said product, 2.2 g of (3S,3aS,4R,7S,7aR) 3-hydroxy-tetrahydro-4,7-methano-isobenzofuran-1-one with a specific rotation of $[\alpha]_D^{20} = -47°$ (c=1% in chloroform) and 25 ml of anhydrous benzene was stirred for 2½ hours at reflux while azeotropically distilling off the water of reaction formed. The mixture was evaporated to dryness under reduced pressure and the residue was crystallized from isopropyl ether to obtain 1.5 g of benzyl (αS,3S,-3aS,4R,7S,7aR) α-(1-oxo-3a,4,7,7a-tetrahydro-1H,3H-7-methano-isobenzofuran-3-yl)-D-prolinate melting at 105° C.

IR Spectrum (CHCl$_3$):

Absorption at 1760$^{-1}$ and 1740 cm$^{-1}$ (carbonyl); at 1588 and 1495 cm$^{-1}$ (aromatic-presence of C—O—C); at 696 cm$^{-1}$ (phenyl).

Circular dichroism (dioxane):

| max. ~223 nm | Δε = −2.7 |
| max. at 248 nm | Δε = +0.13 |
| max. at 252 nm | Δε = +0.13 |

NMR Spectrum (deuterochloroform): Peaks at 6.07-6.4 ppm (5- and 6-ethylenic hydrogens of lactone); at 1.33-1.48 ppm and 1.58-1.73 ppm (hydrogens of 8—CH$_2$ of lactone); at 5.04 ppm (3-hydrogen of lactone); at 3.75-3.87-3.98 ppm (2-hydrogens of proline); at 5.22 ppm (hydrogens α-to phenyl); at 7.37 ppm aromatic hydrogens).

EXAMPLE 4

Benzyl (αR,3R,3aR,4S,7R,7aS)
α-(1-oxo-3a,4,7,7a-tetrahydro-1H,3H-4,7-methano-isobenzofuran-3-yl)-L-prolinate A mixture of 2.4 g of benzyl DL-prolinate hydrochloride, 25 ml of benzene, 5 ml of demineralized water and 1.01 g of triethylamine was stirred at 20° C. for one hour and the decanted organic phase was washed with water, dried and evaporated to dryness under reduced pressure to obtain 2.1 g of benzyl DL prolinate.

A mixture of 2.1 g of latter product, 1.66 of (3R,3aR,4S,7R,7aS) 3-hydroxy-tetrahydro-4,7-methano-isobenzofuran-1-one with a specific rotation of $[\alpha]_D^{20} = +47°$ (c=1% in CHCl$_3$) and 20 ml of benzene was refluxed with stirring for 2½ hours while azeotropically distilling off the water of reaction formed and the mixture was evaporated to dryness under reduced pressure. The residue was crystallized from isopropyl ether to obtain 1.2 g of benzyl (αR,3R,3aR,4S,7R,7aS)α-(1-oxo-3a,4,7,7a-tetrahydro-1H,3H-4,7-methano-isobenzofuran-3-yl)L-prolinate with a melting point of 105° C.

IR Spectrum (CHCl$_3$): Absorption at 1760 cm$^{-1}$–1740cm$^{-1}$ (carbonyl); at 1588 cm$^{-1}$ 1495 cm$^{-1}$ (aromatics—presence of C—O—C); at 696 cm$^{-1}$ (phenyl).

Circular dichroism (dioxane):

| | |
|---|---|
| max. ~220 nm | Δε ~ +2.9 |
| max. at 246 nm | Δε = −0.19 |
| Inflex. towards 251 nm | Δε = −0.18 |

NMR Spectrum (deuterochloroform): Peaks at 6–6.33 ppm (5- and 6-ethylenic hydrogens of lactone); at 1.32–1.47 ppm and 1.58–1.73 ppm (hydrogens of 8—CH$_2$ of lactone); at 4.95–5 ppm (3-hydrogen of lactone); at 3.72–3.83–3.95 ppm (2-hydrogen of proline); at 5.18 ppm (hydrogens α- to phenyl); at 7.4 ppm (aromatic hydrogens).

EXAMPLE 5

Methyl (αR,3R,3aR,4S,7R,7aS)
α-[(1-oxo-3a,4,7,7a-tetrahydro-1H,3H-4,7-methano-isobenzofuran-1-yl)-amino]-phenylpropanoate A mixture of 4.3 g of methyl DL-aminophenylpropanoate hydrochloride, 43 ml of demineralized water, 86 ml of ether and 3 ml of triethylamine was stirred at 20° C. for 10 minutes and the decanted aqueous phase was extracted twice with ether. The combined organic phases were dried and evaporated to dryness under reduced pressure to obtain 3.5 g of methyl DL aminophenylpropanoate.

A mixture of the latter product, 3.2 g of (3R,3aR,4S,7R,7aS) 3-hydroxy-tetrahydro-4,7-methano-isobenzofuran-1-one with a specific rotation of $[\alpha]_D^{20} = +47°$ (c=1% in CHCl$_3$) and 40 ml of benzene was refluxed with stirring for 16 hours while azeotropically distilling off the water of reaction formed and was then evaporated to dryness under reduced pressure. The residue was crystallized from isopropanol to obtain 2.2 g of methyl (αR,3R,3aR,4S,7R,7aS) α-[(1-oxo-3a,4,7,7a-tetrahydro-1H,3H-4,7-methano-isobenzofuran-1-yl)-amino]-phenylpropanoate melting at 120° C.

EXAMPLE 6

Methyl (αS,3S,3aS,4R,7S,7aR)
α-[(1-oxo-3a,4,7,7a-tetrahydro-1H,3H-4,7-methano-isobenzofuran-3-yl)-amino]-phenylpropanoate A mixture of 4.3 g of methyl DL aminophenylpropanoate hydrochloride, 43 ml of demineralized water, 86 ml of ether and 3 ml of triethylamine was stirred at 20° C. for 10 minutes and the aqueous phase was extracted with ether. The combined ether phases were dried and evaporated to dryness under reduced pressure to obtain 8.3 g of methyl aminophenylpropanoate.

A mixture of the 8.3 g of the latter product, 3 g of (3S,3aS,4R,7S,7aR) 3-hydroxy-tetrahydro-4,7-methano-isobenzofuran-1-one with a specific rotation of $[\alpha]_D^{20} = -47°$ (c=1% in CHCl$_3$) and 50 ml of anhydrous benzene was refluxed with stirring for one hour while azeotropically distilling off the water of reaction and was then evaporated to dryness under reduced pressure. The 6.7 g of residue was crystallized from isopropanol to obtain 2.1 g of methyl (αS,3S,3aS,4R,7S,7aR) α-[(1-oxo-3a,4,7,7a-tetrahydro-1H,3H-4,7-methano-isobenzofuran-3-yl)-amino]-phenylpropanoate melting at 120° C. From the filtrate, 1.2 g of the R diastereoisomer were obtained which after recrystallization from isopropyl ether melted at ≃76° C.

IR Spectrum (CHCl$_3$): Absorption at 1743 cm$^{-1}$ (carbonyl); at 3345 cm$^{-1}$ (NH).

NMR Spectrum (deuterochloroform): Peaks at 5.83–6.25 ppm (ethylenic hydrogens of lactone); at 1.27–1.42 ppm and 1.52–1.67 ppm (hydrogens of 8—CH$_2$ of lactone); at 2.33–3.33 ppm (3a- and 7a-hydrogens of lactone); at 4.27–4.32 ppm (3-hydrogen of lactone); at 3.75 ppm (hydrogen α- to amine of phenylalanine); at 2.33–3.33 ppm (hydrogens α- to phenyl); at 3.67 ppm (hydrogens of CH$_3$); at 7.35 ppm (aromatic hydrogens).

EXAMPLE 7

Benzyl D-leucine hydrochloride

A mixture of 2 g of the product of Example 1, 15 ml of demineralized water and 1.5 ml of hydrochloric acid was stirred at 20° C. for one hour and was then heated at 60° C. for one hour and then cooled to 20° C. 15 ml of water were added to the mixture and the mixture was extracted with methylene chloride. The organic phase was washed with aqueous N sodium hydroxide solution and then with water until the wash water was neutral, dried and evaporated to dryness under reduced pressure. The residue was taken up in 10 ml of ether and a current of hydrogen chloride was slowly bubbled through the solution,. The mixture was vacuum filtered to obtain 800 mg of benzyl D-leucine hydrochloride melting at 137° C. and having a specific rotation of $[\alpha]_D^{20} = +3.5°$ (c=1% in 0.1 N hydrochloric acid).

Circular dichroism (dioxane): max. towards 217 nm; Δε=−0.95.

EXAMPLE 8

Benzyl L-leucine hydrochloride

A mixture of 1 g of the product of Example 2, 8 ml of demineralized water and 0.8 ml of hydrochloric acid was stirred at 20° C. for one hour and was then heated at 60° C. for one hour and was cooled at 20° C. The mixture was diluted with 15 ml of water and was then extracted with methylene chloride. The organic phase was washed with aqueous N sodium hydroxide solution and with water until the wash water was neutral, dried and evaporated to dryness under reduced pressure. The residue was taken up in 10 ml of ether and a stream of hydrogen chloride was slowly bubbled therethrough. The mixture was vacuum filtered to obtain 350 mg of benzyl L-leucine hydrochloride melting at 135° C. and having a specific rotation of $[\alpha]_D^{20} = -5.5° \pm 1°$ (c=1% in 0.1 N hydrochloric acid). Circular Dichroism (dioxane): max. at 219 nm; $\Delta\epsilon = +1.0$.

EXAMPLE 9

Methyl D-phenylalaniate hydrochloride

A mixture of 2.2 g of the product of Example 5, 20 ml of demineralized water and 1.7 ml of hydrochloric acid was stirred at 20° C. for 16 hours and the mixture was then iced and vacuum filtered. The aqueous filtrate was saturated with potassium carbonate and the surnagent oil was recovered. The aqueous phase was extracted with ether and the combined oil phase and ether extracts were dried and evaporated to dryness under reduced pressure to obtain 1.2 g of an oil. A mixture of the oil and 20 ml of methanol was cooled to 5° to 10° C. and a current of hydrogen chloride was slowly bubbled therethrough. The mixture was evaporated to dryness under reduced pressure and the thick oil was crystallized from ether to obtain 750 mg of methyl D-phenylalaninate hydrochloride melting at 160° C. and having a specific rotation of $[\alpha]_D^{20} = \simeq 28° \pm 1.5°$ (c=1% in ethanol).

NMR Spectrum (deuterochloroform): Peaks at 3.35–3.43 ppm (hydrogens α- to phenyl); at 4.42 ppm (hydrogen β to phenyl); at 3.7 ppm (hydrogens of CH₃); at 7.28 ppm (aromatic hydrogens).

EXAMPLE 10

Methyl L-phenyl-alaninate

Using the procedure of Example 9, a mixture of 1.5 g of the product of Example 6, 5 ml of water and 1.1 ml of hydrochloric acid was reacted to obtain 509 mg of methyl L-phenylalaninate in the form of an oil with a specific rotation of $[\alpha]_D^{20} = +28.5° \pm 1°$ (c=1.5% in ethanol).

NMR Spectrum (CDCl₃): Peaks at 2.62–3.28 ppm (hydrogens α- to phenyl); at 3.62–3.83 ppm (hydrogen β- to phenyl); at 1.47 ppm (hydrogens of NH₂); at 3.67 ppm (hydrogens of CH₃).

EXAMPLE 11

Methyl (3R,3aR,4S,7R,7aS) α-(1-oxo-3a,4,7,7a-tetrahydro-1H, 3H-4,7-methano-isobenzofuran-3-yl)-L-methioninate A mixture of 0.5 ml of triethylamine, 0.600 g of methyl L-methionine hydrochloride and 10 ml of benzene was stirred at 20° C. for one hour and then 0.500 g of (3R,3aR,4S,7R,7aS) 3-hydroxy-tetrahydro-4,7-methano-isobenzofuran-1-one with a specific rotation of $[\alpha]_D^{20} = +47°$ (c=1% in CHCl₃) were added thereto. The mixture was refluxed for 2 hours while azeotropically removing the water of reaction formed and was then cooled and filtered. The filtrate was evaporated to dryness under reduced pressure to obtain 1.13 g of methyl (3R,3aR, 4S,7R,7aS) α-(1-oxo-3a,4,7,7a-tetrahydro-1H,3H-4,7-methanoisobenzofuran-3-yl)-L-methioninate.

IR Spectrum (chloroform): Absorption at 3348 cm⁻¹ (NH); at 1743 cm⁻¹ (carbonyls); at 1654 cm⁻¹ (—C=C— and C—O—C).

NMR Spectrum (deuterochloroform): Peaks at 2.1 ppm (hydrogens of methyl of —S—CH₃); at 3.7 ppm (hydrogens of methyl of —OCH₃); at 4.7 ppm (3-hydrogen of furane ring); at 6.2 ppm (hydrogens of endocyclic double bond).

EXAMPLE 12

Methyl (3S,3aS,4R,7S,7aR) α-(1-oxo-3a,4,7,7a-tetrahydro-1H, 3H-4,7-methano-isobenzofuran-3-yl)-L-methioninate A mixture of 10 ml of benzene, 0.5 ml of triethylamine and 0.600 g of methyl L-methionine hydrochloride was stirred at 20° C. for one hour and then 0.500 g of (3S,3aS,4R,7S,7aR) 3-hydroxy-tetrahydro-4,7-methano-isobenzofuran-1-one with a specific rotation of $[\alpha]_D^{20} = -47°$ (c=1% in CHCl₃) was added thereto. The mixture was refluxed for 2 hours while azeotropically removing the water of reaction formed and was then cooled and filtered. The filtrate was evaporated to dryness under reduced pressure to obtain 1.18 g of methyl (3S,3aS,4R, 7S,7aR) α-(1-oxo-3a,4,7,7a-tetrahydro-1H,3H-4,7-methano-isobenzofuran-3-yl)-L-methioninate.

IR Spectrum (CHCl₃): Absorption at 3340 cm⁻¹ (NH); at 1745 cm⁻¹ (carbonyls).

NMR Spectrum (deuterochloroform): Peaks at 2.1 ppm (hydrogens of methyl of —SCH₃); at 3.7 ppm (hydrogens of methyl of —OCH₃); at 4.6 ppm (3-hydrogen of furane ring); at 6.23 ppm (hydrogens of endocyclic double bond).

EXAMPLE 13

(3S,3aS,4R,7S,7aR) 3-hydroxy-3a,4,7,7a-tetrahydro-1H,3H-4,7-methano-isobenzofuran-1-one STEP A: Benzyl (αS,3S,3aS,4R,7S,7aR) α-[(1-oxo-3a,4,7,7a-tetrahydro-1H,3H-4,7-methano-isobenzofuran-3-yl)-amino]isohexanoate A mixture of 5.2 g of benzyl L-leucinate, 4 g of (3RS, 3aRS,4RS,7RS,7aRS) 3-hydroxy-3a,4,7,7a-tetrahydro-1H,3H-4,7-methano-isobenzofuran-1-one and 40 ml of anhydrous benzene was refluxed for 90 minutes while azeotropically distilling off the water of reaction formed and was then evaporated to dryness under reduced pressure. The residue was added to isopropyl ether and the mixture was vacuum filtered to obtain 2.3 g of benzyl (αS,3S,3aS,4R,7S,7aR) α-[(1-oxo-3a,4,7,7a-tetrahydro-1H,3H-4,7-methano-isobenzofuran-3-yl)-amino]isohexanoate melting at 95° C.

STEP B: (3S,3aS,4R,7S,7aR) 3-hydroxy-3a,4,7,7a-tetrahydro-1H,3H-4,7-methano-isobenzofuran-1-one 2.2 g of the product of Step A were added to a mixture of 1.8 ml of 22° Bé hydrochloric acid in 18 ml of water and the mixture was heated at 55° C. for 17 hours and was then cooled to 20° C. The mixture was extracted with ethyl acetate and the organic phase was washed with 2 N aqueous sodium hydroxide solution. The alkaline aqueous phase was washed with methylene chloride, with ethyl acetate and was acidified to a pH of 3.5 by addition of 2 N hydrochloric acid. The mixture was extracted with ethyl acetate and the organic phase was washed with water, dried and evaporated to dryness. The residue was taken up in ether and the mixture was vacuum filtered to obtain 0.450 g of (3S,3aS,4R,7S,-7aR) 3-hydroxy-3a, 4,7,7a-tetrahydro-1H,3H-4,7-methano-isobenzofuran-1-one melting at 133° C. and having specific rotation of $[\alpha]_D^{20} = -44°$ (c=1% in benzene).

EXAMPLE 14

A mixture of 0.5 g of benzyl D-leucine hydrochloride, 20 ml of acetic acid and 20 ml of methanol was stirred with palladium under a hydrogen atmosphere until absorption ceased and the mixture was filtered. The filtrate was evaporated to dryness under reduced pressure and the residue was chromatographed over silica gel to obtain D-leucine.

Various modifications of the products and processes of the invention may be made without departing from the spirit or scope thereof and it is to be understood that the invention is intended to be limited only as defined in the appended claims.

What we claim is:

1. A substituted lactone of amino acids in all their possible stereoisomeric forms or mixtures thereof of the formula:

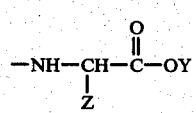

wherein A is selected from the group consisting of an aliphatic hydrocarbon of 2 to 3 carbon atoms optionally containing a double bond, a monocyclic hydrocarbon of 3 to 6 carbon atoms optionally containing one unsaturation, a bicyclic hydrocarbon of 5 to 10 carbon atoms containing one unsaturation,

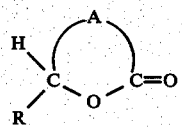

and $X_4$ and $X_5$ are individually selected from the group consisting of hydrogen, fluorine, chlorine, bromine and alkyl of 2 to 6 carbon atoms or taken together with the carbon atoms to which they are attached form a carbon homocycle of 3 to 7 carbon atoms and R is:

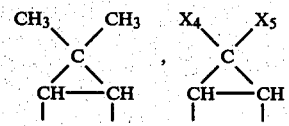

wherein Z is the organic remainder of an amino acid of the group consisting of leucine, phenylalanine and methionine Y is derived from an alcohol selected from the group consisting of primary aliphatic alcohols of 1 to 12 carbon atoms, primary cycloaliphatic alcohols of 4 to 8 carbon atoms and benzyl alcohol.

2. A compound of claim 1 wherein A is an aliphatic hydrocarbon of 2 to 3 carbon atoms.

3. A compound of claim 1 wherein A is an aliphatic hydrocarbon containing one double bond.

4. A compound of claim 1 wherein A is a monocyclic hydrocarbon of 3 to 6 carbon atoms optionally containing an unsaturation.

5. A compound of claim 1 wherein A is a bicyclic hydrocarbon of 5 to 10 carbon atoms optionally containing one unsaturation.

6. A compound of claim 1 wherein A has the formula

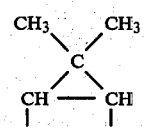

7. A compound of claim 1 wherein A has the formula:

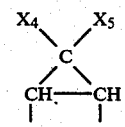

wherein $X_4$ and $X_5$ are individually selected from the group consisting of hydrogen, fluorine, bromine, chlorine and alkyl of 2 to 6 carbon atoms and taken together with the carbon atoms to which they are attached form a carbon homocycle of 3 to 7 carbon atoms.

8. A compound of claim 1 selected from the group consisting of various possible stereoisomeric forms and mixture thereof of benzyl ($\alpha$R,3R,3aR,4S,7R,7aS)$\alpha$-[(1-oxo-3a,4,7, 7a-tetrahydro-1H,3H-4,7-methanoisobenzofuran-3-yl)-amino]-isohexanoate, benzyl ($\alpha$S,3S,-3aS,4R,7S,7aR)$\alpha$-[(1-oxo-3a,4,7,7a-tetrahydro-1H,3H-4,7-methanoisobenzofuran-3-yl)-amino]-isohexanoate, methyl ($\alpha$R,3R,3aR,4S,7R,7aR)$\alpha$-[(1-oxo-3a,4,7,7a-tetrahydro-1H,3H-4,7-methanoisobenzofuran-3-yl)-amino]-phenylpropanoate, methyl ($\alpha$S,3S,3aS,4R,7S,-7aR)$\alpha$-[(1-oxo-3a,4,7,7a-tetrahydro-1H,3H-4,7-methanoisobenzofuran-3-yl)-amino]-phenylpropanoate, methyl (3S,3aS,4R,7S,7aR)$\alpha$-(1-oxo-3a,4,7,7a-tetrahydro-1H,3H-4,7-methanoisobenzofuran-3-yl)-L-methioninate and methyl (3R,3aR,4S,7R,7aS)$\alpha$-(1-oxo-3a,4,7-tetrahydro-1H,3H-4,7-methanoisobenzofuran-3-yl)-L-methioninate.

* * * * *